United States Patent [19]
Bayol et al.

[11] Patent Number: 4,699,900
[45] Date of Patent: Oct. 13, 1987

[54] XYLANE SULFATES, PROCESS FOR THEIR PREPARATION, AND ANTI-THROMBOSIS AND HYPOLIPEMIC ACTIVITY THEREOF

[75] Inventors: Alain Bayol, Tournefeuille; Jacqueline Lansen, Montpellier; Jean P. Maffrand; Jean-Marie Pereillo, both of Portet/Garonne; Eric Vallee, Tournefeuille, all of France

[73] Assignee: Sanofi S.A., Paris, France

[21] Appl. No.: 592,527

[22] Filed: Mar. 23, 1984

[30] Foreign Application Priority Data

Mar. 24, 1983 [FR] France ................... 83 05170

[51] Int. Cl.$^4$ ............ C07H 11/00; C07H 13/12; A61K 31/72; A61K 31/095
[52] U.S. Cl. ........................ 514/54; 514/822; 514/825; 514/886; 514/802; 514/824; 536/118; 536/18.2; 536/4.1; 536/124; 536/18.5; 536/21
[58] Field of Search .............. 424/180, 183; 536/18.2, 536/4.1, 124, 18.5, 21, 118; 514/54, 822, 825, 886, 802, 824

[56] References Cited

U.S. PATENT DOCUMENTS

| | | |
|---|---|---|
| 3,290,263 | 12/1966 | Smythe et al. ............ 536/124 |
| 3,578,657 | 5/1971 | Ricard et al. ............ 536/112 |
| 4,098,995 | 7/1978 | Nair et al. ............ 536/118 |
| 4,122,250 | 10/1978 | Schmer ............ 536/21 |
| 4,221,907 | 9/1980 | Nair et al. ............ 536/118 |
| 4,281,108 | 7/1981 | Fussi ............ 536/21 |
| 4,301,153 | 11/1981 | Rosenberg ............ 424/183 |

FOREIGN PATENT DOCUMENTS

| | | | |
|---|---|---|---|
| 2945595 | 5/1981 | Fed. Rep. of Germany | 536/21 |
| 2543145 | 9/1984 | France | 536/118 |

OTHER PUBLICATIONS

Soria et al., Anticoagulant Activities of a Pentesane Polysulphate: Comparison With Standard Meparin and a Fraction of Low Molecules Weight Heparin, Thrombosis Research 19, 455–63, (1980).
Esquivel et al., Comparison Between Commercial Heparin, Low Molecular Weight Heparin and Pentesan Polysulfate on Memostasis and Platelets in Vivo, Thrombosis Research 28, 389–99, (1982).
Vinazzer et al., Influence on the Clotting System Mechanism of Sodium Pentesan Polysulfate (SP54) in Comparison to Commercial Beef Lung Sodium Heparin, Thrombosis Research 20, 57–68, (1980).
Vinazzer et al., Influence of Heparin of Different Heparin Fractions and of a Low Molecular Weight Heparin Like Substance on the Mechanism of Fibrinolysis, Thrombosis Research 27, 341–52, (1982).
Evans et al., Reaction of Carbohydrates with Methylsulfonyl Chloride in N,N-Dimethylformamide Preparation of Some Methyl 6–chloro–6–deoxyglycosides, Chem Abs 68,87497t, (1968).
Hirano et al., Some N-Acyl Derivatives of N-Desulphated Heparin, Carbohydrate Research 59, pp. 285–288, (1977).

Primary Examiner—Ronald W. Griffin
Attorney, Agent, or Firm—Weiser & Stapler

[57] ABSTRACT

This invention relates to new xylane sulfates having an apparent molar weight comprised between 7000 and 12000.

This invention relates also to a process for their preparation by fractionation, and to the therapeutic application thereof as anti-thrombosis and hypolipemic agents.

18 Claims, No Drawings

XYLANE SULFATES, PROCESS FOR THEIR PREPARATION, AND ANTI-THROMBOSIS AND HYPOLIPEMIC ACTIVITY THEREOF

This invention relates to new xylane sulfates, to a process for their preparation and to their application in human and veterinary medicine.

A conventional practice, when it is desired therapeutically to obtain an anti-coagulant and anti-thrombosis action, is generally to use heparin. The latter, which is a material extracted from animals and which belongs to the class of the acidic mucopolysaccharides is thus administered clinically as anti-coagulant agent, for example by renal dialysis, and as anti-thrombosis agent in the prevention and the treatment of deep venous thrombosis and in the treatment of arterial thrombosis and pulmonary embolism. This therapeutic approach, however, exhibits fairly serious drawbacks, bound on the one hand to the hemorrhagic risks it induces, and on the other hand to the fact that, on administration thereof, thrombopenia is frequently observed to occur, accompanied, in some cases, by thrombo-embolic involvements, and eventually associated with thromboses and other side-effects (shock, alopecia, osteoporosis).

On the other hand, there is also known another sulfated polysaccharide, named SP 54 or PZ 68 in the literature, and which exhibits a clinical efficiency comparable to that of heparin.

The latter compound, which is obtained by semisynthesis from beech wood, exhibits additionally the characteristic of being much less costly than heparin. It is obtained as a mixture of xylane sulfates of different molecular weights. This product, however, is not well defined and different analytical characteristics relating to it are found in the literature.

Thus, VINAZZER et al., report successively an average molecular weight of 2000 (Thromb. Res., 1980, 20, 57–68), then of 3000 (Thromb. Res., 1982, 27, 341–352). C.O. ESQUIVEL et al., (Thromb. Res., 1982, 28, 389–399) describe an average molecular weight of 4000; finally, C. SORIA et al., (Thromb. Res., 1980, 19, 455–463) mention an average molecular weight of 6000.

This discrepancy in the average molecular weights is doubtless due to the analytical methods and to the standards used, together with the lack of precision as to the nature (whether apparent, by weight, or by number) of the molecular weight published.

Applicant has found that this material, which is represented by the following random structural formula:

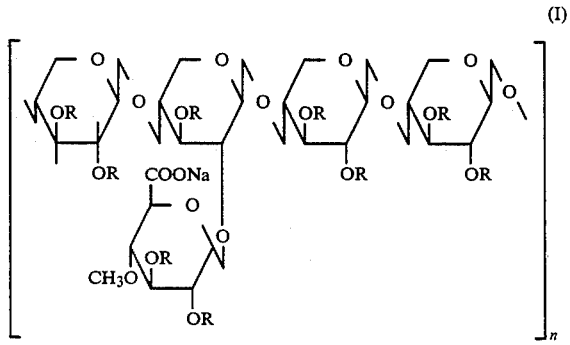

(I)

in which R represents the group —SO$_3$Na or hydrogen in amounts such that the sulfatation degree (S.D.) has a value of 1.81, is defined by the following analytical characteristics:

$\overline{\text{Ma}}$: (apparent average molecular weights): 6000
$\overline{\text{Mn}}$: (number average molecular weights): 5400
$\overline{\text{Mw}}$: (weight average molecular weights): 7000

By "sulfatation degree" is meant the number of —SO$_3$Na groups per monomeric xylose unit.

These molecular weight determinations were confirmed by a determination of the molar weight by formaldehyde titration after oxydation of the reducing ends: M.W. = 6300.

Product SP 54 is also defined by the following characteristics:

Dispersion: D = $\overline{\text{Mw}}/\overline{\text{Mn}}$ = 1.29
Percent uronic acids: 5.8
Percent pentoses: 35.5

The present invention relates to new fractions of xylane sulfates, still represented by formula (I) but defined by an apparent molar weight comprised between 7000 and 12000 and by the following other characteristics:

the sulfatation degree is comprised between 1.5 and 2.0 the percent uronic acid is comprised between 0 and 10 the percent pentose is comprised between 30 and 40, said new fractions retaining a clinical efficiency comparable with that of heparin.

The above analytical characteristics were determined according to the following methods:

1 — Molecular weight determination: Effected by exclusion chromatography through two porous silica columns connected in series. The apparatus used is a HEWLETT PACKARD 1081 B provided with a refractometer (WATERS R 401) and an injector (HP 79841 A). The whole is thermostated at 30° C. The moving phase is prepared according to BARTH H. G. & SMITH D. A. (J. Chromatogr., 1981, 206, 410–415) and is modified by addition of polyethylene glycol to prevent interactions of hydrogen bridge type. The number ($\overline{\text{Mn}}$), weight ($\overline{\text{Mw}}$) and apparent ($\overline{\text{Ma}}$) average molecular weights are calculated from a standard obtained from neutral oligosaccharides and Dextrans.

2 — Number average molecular weight by release of formaldehyde

Xylane: The determination of the absolute number average molecular weight is effected via the method according to VASKOVSKI V. E. & ISAY S. V. (Anal. Biochem., 1936, 30, 25–31) after reduction with sodium borohydride.

Xylane polysulfate: The absolute determination of the number average molecular weight is effected in the same manner as for the xylanes, but after desulfatation of the product.

3 — The dispersion degree (D) is defined by the ratio $\overline{\text{Mw}}/\overline{\text{Mn}}$.

4 — Titration of uronic acids: the method used is the carbazole method according to BITTER T. & MUIR H. H. (Anal. Biochem., 1962, 4, 330–334).

5 — Microtitration of sulfur: after mineralization in a vial according to SHÖNIGER W. (Mikrochim. Acta, 1956, 1, 869–876), the sulfur is titrated conductrimetrically with barium perchlorate.

The sulfatation degree (S.D.) is defined by 5 times the ratio S (moles)/C (moles).

6 — Titration of pentoses: the method used is that via orcinol and ferric chloride in hydrochloric medium (MAJBAUM W. - Z. Physiol. Chem., 1979, 258, 117) using xylose as standard.

This invention includes also within its scope a process for the preparation of the fractions of this invention having formula (I) above, comprising directly submitting product SP 54 to fractionations which may be obtained either by column chromatography, or by ultra-filtration.

Said fractionation may also be effected on the xylanes obtained after desulfatation of SP 54.

According to this modification, the pyridinium salt of SP 54 is submitted to a desulfatation by treatment with dimethylsulfoxide to which is added from 3% to 10% water, at temperatures within the range from 50° C. to 100° C.

The resulting xylane, which is represented by the following structural formula:

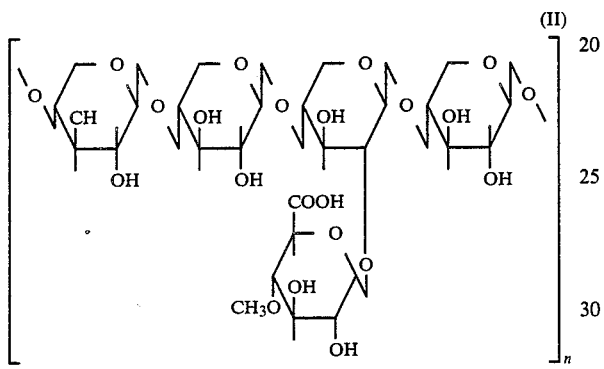

(II)

is defined by the following characteristics:
Ma=3000; $\overline{Mn}$=1950; $\overline{Mw}$=3500; D=1.81
Molecular weight (chemical titration) M.W.=2000
Sulfatation degree (S.D.)=O
Percent uronic acids: 16.5 wt% (as glucuronic acid)
Percent pentoses: 79.5 wt% (as monomeric xylose).

The xylane is then fractionated by solubilization and/or column chromatography, or ultra-filtration. The desired fractions are then selected, which fractions, on sulfatation, lead to the compounds of this invention.

Said sulfatation is effected either with chlorosulfonic acid in the presence of pyridine and optionally of dimethylformamide (DMF), or with the complex sulfur trioxide-trimethylamine within dimethylformamide.

The following non-limiting Examples are given to illustrate this invention.

The SP 54 starting material used in said Examples is that whose analytical characteristics have been defined above, and the analytical characteristics of the final products were determined according to the same methods.

EXAMPLE 1

Desulfatation of xylane polysulfate (SP 54)

A solution of 60 g xylane polysulfate SP 54 (sodium salt) in 80 ml distilled water is eluted with distilled water through a column of 500 ml cation exchange resin (IRN 77 — H+form). The acidic eluates are directly collected in a container containing 32 ml pyridine and placed over an ice-bath.

The resulting solution is freeze-dried. The xylane polysulfate pyridinium salt is recovered as a white powder (68 g).

A solution of 36 g of this pyridinium salt in 100 ml dimethylsulfoxide containing 5% water is heated at 80° C. for 4 hours. After cooling, the reaction medium is poured into 600 ml methanol. The precipitate formed is filtered off, washed with ethanol, and is then redissolved in 100 ml distilled water. The pH of this solution is adjusted to 7.0 by addition of 1 N sodium hydroxide. The resulting solution is then made salt-free (three times) through a preparative Sephadex G 15 gel column (length: 45 cm, diameter: 10 cm), eluted with distilled water. The head fractions which contain the desulfated polymer, free from inorganic sulfate, are collected and then freeze-dried, to give 11.3 g desulfated xylane.

Analytical characteristics
$\overline{Mn}$=1950; $\overline{Mw}$=3500; D=1.81; Ma=3000
Molecular weight (chemical titration)=2000
Sulfatation degree=nil
Percent uronic acids=16.5 wt% (as glucuronic acid)
Percent pentoses=79.5 wt% (as monomeric xylose).

EXAMPLE 2

Fractionation of Xylane Via Solubilization and Sulfatation Fraction of Xylane

Xylane (Example 1; 150 g) is added portionwise, with magnetic stirring, to distilled water (1400 ml) maintained at 50° C. The suspension is allowed to cool to room temperature.

(1) The insoluble xylane fraction is separated by centrifugation, after which it is resuspended in water and freeze-dried.

Weight: 44.1 g; Yield (by weight): 29.4%.
Percent uronic acids: 15.76 wt% (as glucuronic acid).

(2) The soluble fraction of the xylane (supernatant) is in turn freeze-dried, to give 86.5 g cream colored powder.

Yield (by weight): 57.7%.
Percent uronic acids: 17.02 wt% (as glucuronic acid).

Sulfatation of the Water-insoluble Xylane Fraction at 10% w/v)

In a 500 ml three-necked flask, the above xylane (12 g) is dissolved under a nitrogen atmosphere and with magnetic stirring in a mixture of anhydrous pyridine (65 ml) and anhydrous dimethylformamide (65 ml).

Chlorosulfonic acid (28.3 g; 16.2 ml) is added dropwise to the solution maintained at 0° C. On completion of the addition, the reaction medium is heated at 75° C. for 4.5 hours. After cooling, the mixture is poured into 1200 ml methanol. The precipitate formed is filtered off and dissolved in distilled water (100 ml). The solution (pH 3.95) is made basic to pH 8.9 with sodium hydroxide, after which it is evaporated and the residue is taken up into distilled water (50 ml). The pH is controlled (7.6) and the solution is then poured into methanol (1300). The precipitate formed is filtered off, taken up into 100 ml water, and the resulting solution is then treated with 30 g animal black, at 75° C. for 1 hour. The resulting material is filtered, and the procedure is repeated with 30 g animal black. The final solution is filtered through 0.5 micron Millipore, to give 18.2 g of a brown powder.

Analytical characteristics
$\overline{Mn}$=7690; $\overline{Mw}$=10890; D=1.42; Ma=9470
Sulfatation degree=1.72
Percent uronic acids=4.98 wt% (as glucuronic acid)
Percent pentose=30.4 wt% (as monomeric xylose)

EXAMPLE 3

Fractionation of Xylane by Solubilization and Sulfatation

Fractionation of Xylane

Xylane (30 g; Example 1) is suspended in distilled water (240 ml). The medium is adjusted to pH 12 by addition of 6N sodium hydroxide (6 ml) and is then stirred overnight under a nitrogen atmosphere.

The insoluble xylane fraction is collected by centrifugation.

The sediments are taken up into water and the resulting suspensions are freeze dried.
Weight=7.3 g
Percent uronic acids: 12.6 wt% (as glucuronic acid).

Sulfatation reaction of the insoluble xylane at pH 12

The above xylane (7 g) is dissolved, under a nitrogen atmosphere, in a mixture of anhydrous pyridine (25 ml) and anhydrous DMF (25 ml).

To the solution cooled to 0° C. is added dropwise chlorosulfonic acid (16.4 g). On completion of the addition, the reaction mixture is heated at 75° C. for 4.5 hours.

After cooling, the solution is poured into methanol (850 ml). The pyridinium salt of the xylane sulfate is filtered off, rinsed with acetone, and dissolved in 80 ml water (pH 2.85). The solution is made basic to pH 8.1 with 1N sodium hydroxide, and is then evaporated in vacuo. The residue is taken up into 30 ml water (pH 4.5). The pH is adjusted to 11 with 1N sodium hydroxide and the solution is then poured into methanol (1200 ml).

The cream-colored precipitate is filtered off, washed with ether and then dried in vacuo. Weight obtained: 5 g.

Analyctical characteristics
$\overline{Mn}$=7550; $\overline{wM}$=10270; D=1.33; Ma=9120
Sulfatation degree=1.59
Percent uronic acids=6.10 wt% (as glucuronic acid)
Percent pentoses=31.3 wt% (as monomeric xylose).

EXAMPLE 4

Chromatographic Fractionation of the Water-soluble Xylane Obtained in Example 2, Followed by Sulfatation

Fractionation of the xylane

The starting material used in this fractionation consists of the water-soluble xylane fraction as described in Example 2, which is obtained by freezing and freeze-drying the filtrate.

4 g of 10% soluble xylane is chromatographed using 2 columns (length: 75 cm, diameter: 6.0 cm) containing Spherosil XDA 400 porous silica (particle size 40–100 mesh, porosity 80 Å) adapted to a WATERS Prep 500 preparative chromatography apparatus, using as eluent acetic acid at 2% in distilled water; the detector is a differential refractometer.

The refractometrically obtained response curve is cut up into six parts and the corresponding liquid fractions are freeze-dried. The procedure is repeated five times and the homologous fractions are combined.

Cumulative balance of the 6 operations

Fraction 1 — 1.15 g
Fraction 2 — 3.47 g
Fraction 3 — 3.55 g
Fraction 4 — 7.60 g
Fraction 5 — 5.70 g
Fraction 6 — 0.30 g

Sulfatation reaction of fraction 2

Xylane (3.40 g; fraction 2 above) is suspended in anhydrous dimethylformamide (30 ml) under a dry nitrogen atmosphere.

Sulfur trioxide-trimethylamine complex (14 g; 103 mmoles) is added thereto and the reaction medium is heated at 75° C. for 6 hours. After cooling, the reaction medium is evaporated to dryness in vacuo. The resulting residue is taken up into 2N sodium hydroxide (52 ml) and the solution obtained is again evaporated to dryness. The residue is dissolved in distilled water (70 ml) and the pH (initially at 5.6) is adjusted to 8.0 by addition of 2N sodium hydroxide (15 ml); after evaporation to dryness, the residue is taken up into 70 ml water and the resulting solution (pH 7) is filtered through 5 μ Millipore, and then chromatographed through 2 porous silica columns (eluent: distilled water) to remove the inorganic salts.

The eluate fraction corresponding to xylane sulfate is freeze-dried, to give 5.30 of a cream colored powder.

Analytical characteristics
$\overline{Mn}$=9260; $\overline{Mw}$=10380; D=1.12; Ma=9790
Sulfatation degree=1.78
Percent uronic acids=8.25 wt% (as glucuronic acid)
Percent pentoses=32 wt% (as monomeric xylose).

EXAMPLE 5

Fractionation by Ultrafiltration of the Water-soluble Xylane Obtained in Example 2, and Subsequent Sulfatation

Fractionation of the xylane

The water-soluble xylane fraction (25 g) is dissolved, as described in Example 2, in distilled water (1000 ml). This solution is treated in an ultrafiltration system provided with a cartridge of hollow fibers H 1P10-8 of AMICON ® brand (cut-off threshold: 10,000 daltons), at a pressure of 1 Bar or less.

The operation is complete when 5000 ml water have been taken-up by the system.

The ultrafiltration retained material is then removed from the system, and is then freeze-dried.

4.4 g of a cream-colored powder are obtained after drying (a yield of 17.6% with respect to the original amount).

Sulfatation reaction 3 g of the xylane isolated above are suspended in anhydrous dimethylformamide (30 ml) under an atmosphere of dry nitrogen. Sulfur trioxide-trimethylamine complex (7.90 g; 56.7 mmoles) is added stepwise to the suspension. The reaction mixture is then heated at 75° C. for 5.5 hrs.

After cooling, 1N sodium hydroxide (80 ml) is added thereto, and the material is then evaporated to dryness under the vacuum of a water-pump.

The residue is taken up into distilled water (30 ml), the pH of the resulting solution is brought up from 5 to 12 by addition of 1N sodium hydroxide (20 ml), and the material is then concentrated in vacuo. The evaporation residue is taken up into distilled water (30 ml); the pH of the resulting solution has a value of 9. 1N Hydrochloric acid is then added to adjust the pH to 7, after which the solution is made salt-free by elution through a Sephadex G 15 column (L=90 cm; φ=4.4 cm)(refractometric detection).

The eluate fraction containing the xylane polysulfates is collected and then freeze-dried. A white powder (4.3 g) is collected after drying under high vacuum, at room temperature.

Analytical characteristics
$\overline{Mn}$=9035; $\overline{Mw}$=10550; D=1.17; Ma=9840
Sulfatation degree: 1.64.

EXAMPLE 6

Fractionation by Ultrafiltration of the Xylane Obtained in Example 2, with Subsequent Sulfatation

Fractionation of the xylane

A solution of 15 g of the water-soluble xylane fraction obtained according to Example 2, in 1500 ml distilled water, is submitted to an ultrafiltration using a system provided with a cartridge of hollow fibers having a cut-off threshold of 5000 (type H 1P5-20, AMICON® brand), under a pressure of ≦1 Bar, while distilled water is continuously provided.

The operation is completed when 8000 ml distilled water have been used.

The solution retained by the hollow fibers is concentrated, after which it is removed from the system, and is then freeze-dried, to give 4.5 g (30% of the original amount) of a cream-colored powder.

Sulfatation reaction 4 g of the xylane obtained above are suspended in 60 ml anhydrous dimethylformamide, under an atmosphere of dry nitrogen. Sulfur trioxide-trimethylamine complex (10.5 g; 7.5 mmoles) is added stepwise thereto, and the mixture is heated at 80° C. for 6 hours. After cooling down to room temperature, 1N sodium hydroxide (80 ml) is added to the reaction mixture which is then evaporated to dryness in vacuo.

The residue is taken up into distilled water (50 ml). The pH of the resulting solution is adjusted from 6.25 to 12.4 by addition of 1N sodium hydroxide (5 ml). The solution is evaporated to dryness, in vacuo, after which the residue is taken up into distilled water (50 ml). The pH is adjusted down from 10.7 to 7.35 by addition of 1N hydrochloric acid (1.35 ml). The solution is then submitted to an ultrafiltration using a system provided with hollow fibers having a cut-off threshold of 5000 (type H 1P5-20, AMICON brand), to remove the residual inorganic salts, under a pressure of 1 Bar or less.

The solution retained by the system is freeze-dried, to give 6.7 g of a white powder.

Analytical characteristics
$\overline{Mn}$=8340; $\overline{Mw}$=11310; D=1.36; Ma=9260
Sulfatation degree=1.55
Percent uronic acids: 8.12 wt% (as glucuronic acid)
Percent pentoses: 38.3 wt% (as monomeric xylose).

EXAMPLE 7

Fractionation by Precipitation of the Water-Soluble Xylane Fraction Obtained in Example 2, and Subsequent Sulfatation

Fractionation of the xylane 40 g of the water-soluble xylane fraction obtained in Example 2 are dissolved in 400 ml distilled water, with magnetic stirring.

95% Ethanol (200 ml) is added to this solution, with continued stirring.

After stirring for ½ hour, the resulting suspension is centrifuged. The centrifugation sediments are decanted, taken up into water and recovered by freeze-drying, to give 2.4 g of a cream-colored product.

Sulfatation reaction 2 g of the xylane fraction obtained above are suspended in 25 ml anhydrous dimethylformamide, with stirring, under a dry nitrogen atmosphere.

Sulfur trioxide-trimethylamine complex (5.25 g; 0.037 moles) is added to this mixture, which is then heated at 75° C. for 5.5 hours. After cooling to room temperature, 1N sodium hydroxide (52 ml) is added to the reaction medium, which is then evaporated to dryness, in vacuo. The resulting residue is taken up into distilled water (40 ml) and the pH of the solution is adjusted from 6 to 13 by addition of 1N sodium hydroxide (10 ml). After evaporation to dryness, in vacuo, the residue is taken up into distilled water (40 ml). This solution is adjusted to pH 7 with 1N hydrochloric acid; it is then filtered through 8 μ Millipore, and is finally eluted through a Sephadex G15 column to remove the inorganic residues. The eluate fraction corresponding to the xylane polysulfate is collected and freeze-dried, to give 3.75 g of a white powder.

Analytical characteristics
$\overline{Mn}$=10040; $\overline{Mw}$=11800; D=1.18; Ma=10685
Sulfatation degree=1.72

EXAMPLE 8

Fractionation by Solubilization of the Xylane Obtained in Example 1, and Subsequent Sulfatation

Fractionation of the xylane 150 g of xylane obtained according to the process described in Example 1 are added, with magnetic stirring, to 1000 ml distilled water thermostatically maintained at 50° C. After stirring for 8 hours, the material is allowed to cool to room temperature, and the insoluble fraction is recovered by centrifugation.

The centrifugation residues are taken up into a small amount of distilled water, and are then combined and freeze-dried, to give 38.3 g of a cream-colored powder.

Sulfatation reaction 5 g of the xylane obtained above are suspended in 50 ml anhydrous dimethylformamide, with magnetic stirring and under a dry nitrogen atmosphere. 13.5 g (94.5 mmoles) of sulfur trioxide-trimethylamine complex are added to the suspension, and the reaction medium is heated at 75° C. for 8 hours. After cooling down to room temperature, the mixture is made basic with 1N sodium hydroxide (150 ml) to pH 8, and is then evaporated to dryness in vacuo. The residue is taken up into 50 ml distilled water and the pH of the solution is adjusted from a value of 8.3 to a value of 6.85 by addition of 0.9 ml 1N hydrochloric acid.

The solution is then submitted to an ultrafiltration using a hollow fiber system provided with a cartridge having a cut-off threshold of 5000 Daltons,(of H 1-P5-20 type, AMICON brand), under a pressure of 1 bar or less, to remove the inorganic salts.

The material retained is then freeze-dried, to give 7.9 g of a cream-colored powder.

Analytical characteristics:
$\overline{Mn}$=6670; $\overline{Mw}$=11430; D=1.72; Ma=9390

Sulfatation degree: 1.79
Percent uronic acids: 5.1 wt% (as glucuronic acid)
Percent pentoses: 39.9 wt%(as monomeric xylose).

EXAMPLE 9

Fractionation of Xylane Polysulfate (SP 54) by Chromatography

A chromatographic column (L=60 cm; $\phi$=4.4 cm) is packed with ion exchange cellulose (WHATMAN DE 52) pre-conditioned with a buffer mixture (AcONa 0.2 M, AcOH 0.06 M) at pH 6.5.

The flow rate of the eluent is controlled with a peristaltic pump, and analysis of the eluates is effected with an U.V. detector ($\lambda$=254 nm).

20 g of xylane polysulfate (SP 54) dissolved in 60 ml of the original buffer are injected through the column, after which elution is effected with the same buffer until stabilization of the product on the exchange gel.

Elution is then carried out with a succession of sodium chloride solutions, of increasing concentrations.

The eluate fractions corresponding to each eluent solution are collected and freeze-dried.

Successive eluents used:
0.3 M NaCl — F1
0.4 M NaCl — F2
0.5 M NaCl — F3
0.6 M NaCl — F4
0.7 M NaCl — F5
0.8 M NaCl — F6
0.9 M NaCl — F7
1.0 M NaCl — F8
1.2 M NaCl — F9

Each fraction is made salt-free by chromatography through porous silica column (eluent:distilled water) and the fraction corresponding to the purified polysaccharide sulfates is recovered by freeze-drying. The procedure is repeated a number of times to obtain sufficient amounts of each product, by combining the homologous fractions. Overall balance of four such operations:

| | | |
|---|---|---|
| F1 | 4.2 g | (0.3 M NaCl buffer) |
| F2 | 5.3 g | (0.4 M NaCl buffer) |
| F3 | 4.65 g | (0.5 M NaCl buffer) |
| F4 | 5.25 g | (0.6 M NaCl buffer) |
| F5 | 6.45 g | (0.7 M NaCl buffer) |
| F6 | 6.30 g | (0.8 M NaCl buffer) |
| F7 | 6.65 g | (0.9 M NaCl buffer) |
| F8 | 3.3 g | (1.0 M NaCl buffer) |
| F9 | 0.65 g | (1.2 M NaCl buffer). |

Analytical characteristics of the fractions selected

| | $\overline{Mn}$ | $\overline{Mw}$ | Disp. | Ma | S.D. | % Uronic acid | % pentoses |
|---|---|---|---|---|---|---|---|
| F6 | 8120 | 9090 | 1.2 | 8790 | 1.58 | 5.38 | 38.04 |
| F7 | 10500 | 12050 | 1.14 | 10960 | 1.71 | 4.70 | 38.66 |
| F8 | 11320 | 12660 | 1.12 | 11500 | 1.69 | 4.68 | 38.04 |
| F9 | 11740 | 13240 | 1.12 | 11940 | 1.71 | 2.06 | 35.49 |

EXAMPLE 10

Fractionation of Xylane Polysulfate (SP 54) by Ultrafiltration

A solution of xylane polysulfate (SP54; 30 g) in distilled water (600 ml) is submitted to an ultrafiltration using a system provided with an AMICON SYMS membrane (cut-off threshold: 5000) and with a distilled water reserve supply. The working pressure is insured by nitrogen under a pressure of 4 Bars. After 800 ml ultrafiltrate have been collected, the contents of the cell are recovered and freeze-dried, to give 11.75 g of a white powder (i.e., 39.1% of the original weight).

Analytical characteristics
$\overline{Mn}$=7180; $\overline{Mw}$=9500; D=1.32; Ma=7800
Sulfatation degree: 1.71.

EXAMPLE 11

Fractionation of Xylane Polysulfate (SP 54) by Chromatography

Xylane polysulfate (SP 54; 3 g) in distilled water (10 ml) is injected through a chromatographic system comprising two serially connected columns (L=75 cm; $\phi$=6 cm) packed with Spherosil XOA 400 porous silica (particle size 40–100 mesh, porosity 80 Å) with an eluent (distilled water) flow rate of 40 ml/mn.

Detection is effected with a differential refractometer.

The eluent portion which contains the xylane polysulfate is fractionated into four volumes.

The procedure is repeated 15 times and the homologous fractions are combined and freeze-dried.

Balance of the 16 operations:

| | | |
|---|---|---|
| F1 | 5.9 g | (yield: 12.3 wt %) |
| F2 | 5.7 g | (yield: 12 wt %) |
| F3 | 13.6 g | (yield: 28.3 wt %) |
| F4 | 15.74 g | (yield: 32.8 wt %). |

Analytical characteristics of the higher molecular weight fraction (Fraction 1)
$\overline{Mn}$=9370; $\overline{Mw}$=11180; D=1.19; Ma=9840
Sulfatation degree=1.73.

EXAMPLE 12

Fractionation of Xylane Polysulfate (SP 54) by Ultrafiltration

A solution of xylane polysulfate (SP 54; 20 g) in distilled water (300 ml) is submitted to an ultrafiltration through a system provided with hollow fibers having a cut-off threshold of 5000 Daltons (type H 1 P5-20, AMICON brand), under a pressure of 1 Bar or less.

After absorption by the system of 1500 ml distilled water, the solution of the higher molecular weights retained by the hollow fibers is drawn out of the system and freeze-dried, to give 6.7 g of a white powder (yield: 33.5% with respect to the original amount)

Analytical characteristics
$\overline{Mn}$=7160; $\overline{Mw}$=8820; D=1.23 Ma=7390
Sulfatation degree=1.71

EXAMPLE 13

Fractionation of Xylane Polysulfate (SP 54) by Ultrafiltration

A solution of xylane polysulfate (SP 54; 60 g) in distilled water (1000 ml) is submitted to an ultrafiltration through a system provided with hollow fibers having a cut-off threshold of 10,000 Daltons (type H1P10-8, AMICON brand), under a pressure of 1 Bar or less.

After absorption by the system of 5000 ml distilled water, the solution of the higher molecular weights retained by the hollow fibers is drawn out of the system and freeze-dried, to give 3.6 g of a white powder (yield: 6% by weight of the original amount).

Analytical characteristics $\overline{Mn} = 9500$; $\overline{Mw} = 11,720$; $D = 1.20$ Sulfatation degree = 1.63

EXAMPLE 14

Fractionation of Xylane Polysulfate (SP 54) by Ultrafiltration

A solution of xylane polysulfate (SP 54; 30 g) dissolved in 1M $NaNO_3$ (500 ml) is submitted to an ultrafiltration through the system already used in Example 10, provided with an identical membrane having a cut-off threshold of 5000 Daltons (5YM5 type, AMICON btand), but the reserve eluent container is filled with a 1M sodium nitrate solution.

The operating pressure is provided by nitrogen under a pressure of 4 Bars.

After collecting 1600 ml ultrafiltrate, the contents of the cell are recovered, and are then injected stepwise over a preparative column (L=45 cm, $\phi$=10 cm) packed with Sephadex G25, eluted with distilled water, to remove the sodium nitrate.

The eluent fractions containing the purified polymers are combined and freeze-dried, to give 6.87 g of a white powder (yield: 22.9% by weight of the original amount)

Anayltical characteristics $\overline{Mn} = 9850$; $\overline{Mw} = 11815$; $D = 1.20$ Sulfatation degrees: 1.70.

EXAMPLE 15

Fractionation of Xylane Polysulfate (SP 54) by Ultrafiltration

A solution of xylane polysulfate (SP 54; 1.2 kg) in deionized water (18 litres)(concentration: 6.66 wt%) is submitted to an ultrafiltration through a system provided with a cartridge of hollow fibers ROMICON 22-20 PM-5 (length 63 cm; developed surface of the fibers 2.4 $cm^2$) and with a deionized water inlet (to maintain the volume of the solution to be treated at a constant level throughout the operation).

The recycle pump of the solution is set to provide an average pressure of 1.45 Bar and an average permeate rate of 150 ml per minute. When 42 litres of ultrafiltrate (2.5 volumes with respect to the volume of the original solution) have been obtained, the retained material is drawn out of the system, and the pump body and the inner portion of the hollow fibers are rinsed with 3 litres deionized water.

The solution (21 litres) consisting of the retained material and the rinsing solution is then re-treated with the system which is, at that time, provided with a cartridge of hollow fibers ROMICON 30-20 PM-10 (length 63 cm, developed surface of the fibers 2.8 $cm^2$).

In a first step, the solution is concentrated to half volume (10.5 litres ultrafiltrate are collected). The water inlet is opened and the ultrafiltration is conducted under a constant volume of retained material at a pressure of 1.4 Bar, until a total volume of 52 litres ultrafiltrate (including the concentration ultrafiltrate) has been obtained. This final permeate (52 litres) is then concentrated to 22 liters using the same system provided with a ROMICON 15-43 PM2 cartridge (length 63 cm, developed surface of the fibers 1.4 $cm^2$) and subsequently freeze-dried, to give 315 g of a white powder (yield: 26.2 wt% with respect to the original amount).

Analytical characteristics:

$\overline{Mn} = 6700$; $\overline{Mw} = 7850$; $D = 1.17$; $Ma = 7500$

Sulfatation degree = 1.76.

The results of pharmacological tests reported below demonstrate the useful properties of the products of this invention, i.e., the different fractions obtained from SP 54.

Therefore, the invention includes also within its scope a therapeutic composition having, in particular, anti-thrombosis and hypolipemic properties, comprising, as active ingredient, at least one of the fractions prepared by the process of this invention and having the formula (I).

The pharmacological investigation related to the anti-coagulant, anti-thrombosis, fibrinolytic, lipolytic actions, and to the bleeding time; said investigations were effected comparatively with heparin and with SP 54, respectively.

The anti-coagulant action is determined by the activated cephalin time (CAEN J., LARRIEU M.J., SAMAMA M., in: L'hémostase: méthodes d'exploration et diagnostic pratique. Ed. : l'Expansion Scientifique Française, 1975, p. 169).

The activated cephalin time (ACT), is a measure of the re-calcification of blood-platelet free plasma in the presence of an optimum amount of lipids (cephalin) and of Celite which activates in a standardized manner the factors of the contact phase (factors XII, XI, IX). Therefore, it is a measure of the formation of endogenous prothrombinase with the exception of the blood-platelet factors substituted with cephalin.

The anti-thrombosis action is evaluated by the anti Xa activity (YIN E. T., WESSLER S., BUTLER J. V., J. Lab. Clin. Med., 1973, 81, 298–310). The yin time is a measure of the neutralizing action of SP 54 and its fractions with respect to factor Xa in the presence of excess antithrombine III and factor Xa.

The anti-thrombosis activity is also evaluated by means of a standard test of experimental thrombosis on a silk thread introduced in an arterio-venous shunt in rat (UMETSU T., SANAI K., Thromb. Haemost., 1978, 39, 74–83).

The fibrinolytic activity is measured by the lysis time of plasmatic euglobulins (KLUFT C., Haemostasis, 1976, 5, 136).

The lysis time of the plasmatic euglobulins is a sensitized method which permits the evaluation of the overall fibrinolytic action of SP 54 and its fractions in the absence of the physiological inhibitors of fibrinolysis, removed by dilution and acidification of the plasma.

The lipolytic activity is determined by the circulating lipoprotein lipase activity (NIKKILA E. A., HUTTUNEN J. K., ENHOLM C., Metabolism, 1977, 26, 179).

The determination of the circulating lipoprotein lipase activity is an indirect measure of the impact of SP 54 and its fractions on the catabolism of triglycerides (clarifying action). The enzymic activity is determined by its capacity to hydrolyze the 14C-trioleine substrate to 14C-oleic acid.

The bleeding time is determined after cross section of rat's tail (STELLA L., DONATI M. B., DE GAETANO G., Thromb. Res., 1975, 7, 709–716).

Sprague Dawley male rats (body weight 200–300 g) were used for the different experiments.

The animals were anesthetized with pentobarbital (50 mg/kg) by the intraperitoneal route, and the test materials were administered intravenously (vein of the penis). 15 Minutes after administration of the test materials, blood samples were taken from the abdominal aorta and were made incoagulable with a 3.8% trisodium citrate solution (1 volume anticoagulant per 9 volumes blood) or with heparin (25U/ml of blood).

Immediately after blood taking, the samples were centrifuged at 2000×g for 15 minutes at 4° C., to prepare the citrated plasma used for the various determinations.

The results obtained are tabulated in Tables 1 and 2. Their statistical analysis was effected:
(a) according to the STUDENT test (comparative group: SP 54)
(b) according to the MANN & WHITNEY U-test (comparative group: reference group).

In Tables 1 and 2:
NS: not significant
X: p 0.05
XX: p 0.01
XXX: p 0.001

TABLE 1

| Test Materials | Ma | BLOOD COAGULATION (a) A. C. T. 2.5 mg/kg/IV % extension | A. C. T. 5 mg/kg/IV % extension | ANTI-Xa 5 mg/kg/IV % extension |
|---|---|---|---|---|
| SP 54 | 6 000 | 104 | 200 | 25 |
| HEPARIN | 20 000 | 1 178 | incoagulable | 506 |
| Example 2 | 9 470 | 129* | 298* | 57** |
| Example 3 | 9 120 | 155** | 512*** | 183*** |
| Example 4 | 9 790 | 178*** | 442*** | 91*** |
| Example 5 | 9 840 | 214*** | 1 090*** | 79** |
| Example 6 | 9 260 | 168** | 1 100*** | 112*** |
| Example 7 | 10 685 | 190*** | 591*** | 70*** |
| Example 8 | 9 380 | 134* | 461*** | 76** |
| Example 9 F6 | 8 790 | 102 (NS) | 180 (NS) | 67** |
| Example 9 F7 | 10 960 | 186*** | 442*** | 74** |
| Example 9 F8 | 11 500 | 212*** | 631*** | 104*** |
| Example 9 F9 | 11 940 | 243*** | 723*** | 112*** |
| Example 10 | 7 890 | 158*** | 486*** | 80*** |
| Example 11 | 9 840 | 248*** | 844*** | 68** |
| Example 12 | 7 390 | 149 (NS) | 369** | 67** |
| Example 13 | 10 780 | 281*** | 1 100*** | 126*** |
| Example 14 | 10 190 | 173** | 634*** | 84** |
| Example 15 | 7 500 | 171* | 352 (NS) | 41* |

Thus, the useful anti-thrombosis and hypolipemic properties of the products of this invention are apparent from the investigations reported above.

Indeed, while the therapeutic composition of this invention has a considerable anti-thrombosis action, its anticoagulant effect is low, thus reducing the hemorrhagic risks induced by drugs of this type.

The therapeutic composition of this invention may be formulated as orally, parenterally, rectally and topically administrable preparations.

Each unit dose contains advantageously 0.010-0.250 g active ingredient, the daily regimen varying from 0.010 g to 0.500 g, depending on the age of the patient and the severity of the disease treated.

Non-limiting Examples of pharmaceutical formulations of the products of this invention are given below:

1 TABLETS
| Fraction no. 2 | | 0.050 g |
| Excipient | sufficient, to make | 1 tablet |

2 CAPSULES
| Fraction no. 6 | | 0.075 g |
| Excipient | Sufficient, to make | 1 capsule |

3 INJECTABLE AMPOULES
| Fraction no. 8 | | 0.100 g |
| Isotonic solvent | sufficient to make | one 2 ml ampoule |

4 OINTMENT
| Fraction no. 10 | | 0.150 g |
| Excipient | sufficient to make | one 30 g tube |

In view of their action on the various stages of blood coagulation and of fibrinolysis, said therapeutic compositions are advantageously used for extended and repeated cures in the preventive or curative treatment of venous or arterial thrombo-embolic involvements in cases of phlebitis, pulmonary embolism and other clinical situations of the same type, angina pectoris, myocardial infarction, chronic arteritis of the lower limbs, superficial circulatory disorders, and ulcers of the legs.

They are also useful for the prevention of thromboses in the extra-corporal circuits (renal hemodialysis).

In addition, their action on lipoprotein-lipase (clarifying factor) makes them particularly useful in the treatment of atherogenous dyslipemia.

TABLE 2

| Test Materials | Ma | FIBRINOLYSIS (a) 2.5 mg/kg/IV % activation | LIPOPROTEIN LIPASE (a) 2.5 mg/kg/IV % release | THROMBOSIS SILK THREAD (b) 5 mg/kg/IV % inhibition | BLEEDING TIME (b) 5 mg/kg/IV Extension factor |
|---|---|---|---|---|---|
| SP 54 | 6000 | 48 | 59 | −53** | ×1.6* |
| HEPARIN | 20000 | 40 | 64 | −57** | >×10** |
| Example 2 | 9470 | 57** | 84** | −58** | ×1.8* |
| Example 3 | 9120 | 57** | 105*** | −85** | ×4.2** |
| Example 4 | 9790 | 65*** | 101*** | −96** | |
| Example 5 | 9840 | 61*** | 86** | −86** | |
| Example 6 | 9260 | 50 (NS) | 97*** | −26 (NS) | ×3.0** |
| Example 7 | 10685 | 37** | 84** | | |
| Example 8 | 9380 | 46 (NS) | 77** | −100** | >×10** |
| Example 9 F6 | 8790 | 36** | 64 (NS) | | |
| Example 9 F7 | 10960 | 41** | 77*** | | |
| Example 9 F8 | 11500 | 60*** | 92*** | −42** | ×1.4 (NS) |
| Example 9 F9 | 11940 | 62*** | 115*** | | |
| Example 10 | 7890 | 58** | 160*** | −85** | ×2.1* |
| Example 11 | 9840 | 63*** | 78** | −79** | ×2.7* |
| Example 12 | 7390 | 42 (NS) | 96*** | | |
| Example 13 | 10780 | 48 (NS) | 94*** | | |
| Example 14 | 10190 | 35** | 85** | | |
| Example 15 | 7500 | 41 (NS) | 38* | −54*** | ×2.2* |

Finally, said compositions may also be used advantageously in the treatment of certain inflammatory diseases such as rheumatoid arthritis, arthrosis and osteoarthritis.

We claim:

1. Xylane sulfates having a sulfatation degree between 1.5 and 2.0 and an apparent molecular weight from about 7,000 to about 12,000.

2. The xylane sulfates of claim 1 having uronic acid content between 0 and 10 percent.

3. The xylane sulfates of claim 1 having a pentose content between 30 and 40 percent.

4. Xylane sulfates having a sulfatation degree between 1.5 and 2.0, an apparent molecular weight from about 7,000 to about 12,000 a uronic acid content between 0 and 10 percent and a pentose content between 30 and 40 percent.

5. A pharmaceutical composition effective as an antithrombotic, anticoagulant, and hypolipemic which comprises a pharmaceutically acceptable carrier and in a therapeutically effective amount, the xylane sulfates of claim 1.

6. The pharmaceutical composition of claim 5 which is suitable for oral, parenteral, rectal or topical administration.

7. The pharmaceutical composition of claim 5 which is in unit dosage from wherein each unit dose contains from 0.010 g to 0.250 g of the xylane sulfates of claim 1.

8. A method for the treatment of venous thrombosis in a host which comprises administering to said host the composition of claim 5.

9. A method for the treatment of arterial thrombosis in a host which comprises administering to said host the composition of claim 5.

10. A method for effecting an anticoagulant response in a host which comprises administering to said host the composition of claim 5.

11. A method for the treatment of atherogenous dyslipemia in a host which comprises administering to said host the composition of claim 5.

12. A method for the treatment of inflammation in a host which comprises administering to said host the composition of claim 5.

13. A method for the treatment of rheumatoid arthritis, arthrosis or osteoarthritis in a host which comprises administering to said host the composition of claim 5.

14. The method for the treatment of a condition selected from the following: venous thrombosis, dyslipemia, inflammation, arthritis and for causing anticoagulation in a host in need thereof which comprises administering the compound of claim 1 to said host and causing an alleviation of said condition.

15. A pharmaceutical composition effective as an antithrombotic which comprises a pharmaceutically acceptable carrier and in a therapeutically effective amount, the xylane sulfates of claim 1.

16. The pharmaceutical composition of claim 15 which is suitable for oral, parenteral, rectal or topical adminstration.

17. The pharmaceutical composition of claim 15 which is in unit dosage form wherein each unit dose contains from 0.010 g to 0.250 g of the xylane sulfates of claim 1.

18. The method for the treatment of venous thrombosis in a host in need thereof which comprises administering the compound of claim 1 to said host and causing an alleviation of venous thrombosis.

* * * * *